US006969602B1

(12) United States Patent
Danforth et al.

(10) Patent No.: US 6,969,602 B1
(45) Date of Patent: Nov. 29, 2005

(54) **PRODUCTION OF AN IMMUNOVARIANT STRAIN OF *EIMERIA MAXIMA* CONTRIBUTES TO STRAIN CROSS-PROTECTION WITH OTHER *EIMERIA MAXIMAS***

(75) Inventors: Harry D. Danforth, Severn, MD (US); M. Aggie Fernando, Waterloo (CA); John R. Barta, Guelph (CA)

(73) Assignees: The United States of America as represented by the Secretary of the Agriculture, Washington, DC (US); University of Guelph, Guelph (CA)

( * ) Notice: Subject to any disclaimer, the term of this patent is extended or adjusted under 35 U.S.C. 154(b) by 0 days.

(21) Appl. No.: 09/838,382

(22) Filed: Apr. 20, 2001

(51) Int. Cl.[7] .......................... C12N 1/10; G01N 33/53; A61K 39/00; A61K 39/38; A61K 39/002
(52) U.S. Cl. ........................ 435/258.1; 424/184.1; 424/191.1; 424/271.1; 435/7.22; 435/258.1; 435/258.4; 435/342; 530/388.6; 530/822
(58) Field of Search ..................... 424/191.1, 184.1, 424/271.1; 435/722, 258.4, 342, 7.22, 258.1; 530/388.6, 822

(56) References Cited

OTHER PUBLICATIONS

Barta et al. 1998. International J. for Parasitology. 28:482-492.*

Martin et al. 1997. International J. for Parasitology. 27(5): 527-533.*

Fernando, M.A., et al., "Identification and Biological Characterization of Immunologically Distinct Strains of *Eimeria maxima* ", Convencion Nacional ANECA First Annual Symposium on Avian Coccidiosis, Acapulco, Mexico, Apr. 22-28, 2001.

Barta, J.R., et al., "Analysis of Infraspecific Variation Among Five Strains of *Eimeria maxima* from North America", *International J. for Parasitology*, vol. 28, pp. 485-492, 1998.

Martin, A.G., et al., "Analysis of Immunological Cross-Protection and Sensitivities to Anticoccidial Drugs Among Five Geographical and Temporal Strains of *Eimeria maxima*", *International J. for Parasitology*, vol. 27, (5), pp. 527-533, 1997.

Danforth, H., "Use of Live Oocyst Vaccines in the Control of Avian Coccidiosis: Experimental Studies and Field Trials", *International J. for Parasitology*, vol. 28 pp. 1099-1109, 1998.

* cited by examiner

*Primary Examiner*—Lynette R. F. Smith
*Assistant Examiner*—Ja-Na Hines
(74) *Attorney, Agent, or Firm*—John D. Fado; Evelyn M. Rabin

(57) ABSTRACT

An immunovariant strain of *Eimeria maxima* was isolated. Vaccines incorporating the immunovariant strain are effective in eliciting immunological protection against coccidial infection.

2 Claims, 6 Drawing Sheets

PRODUCTION OF AN IMMUNOVARIANT STRAIN OF *EIMERIA MAXIMA* CONTRIBUTES TO STRAIN CROSS-PROTECTION WITH OTHER *EIMERIA MAXIMAS*

BACKGROUND OF THE INVENTION

1. Field of the Invention

This invention is in the field of avian coccidiosis and relates to effective live oocyst vaccines for coccidiosis and their development through incorporation of new immunovariant derived strains of *Eimeria maxima*.

2. Description of the Relevant Art

Coccidiosis is an intestinal disease caused by avian protozoan parasites and is estimated to cost the U.S. poultry industry over $400 million annually. The major component in coccidiosis control in the poultry industry since the 1950s has been the use of anticoccidial compounds. These compounds, when used in carefully designed prophylactic treatment programs, are efficient in disease control. However, all anticoccidial compounds now cleared for use in chickens are showing diminished efficacy due to increased parasite drug resistance. No new anticoccidials are currently being cleared for use. This has resulted in a re-examination of another type of coccidial control, the use of live oocyst-based vaccines.

Vaccination against coccidiosis is not a new concept; it has been used by the poultry industry since the early 1950s. The four dominant commercial vaccines used by the poultry industry, COCCIVAC®, IMMUCOX®, Livacox, and PARACOX®, typically incorporate several species and strains of *Eimeria*. Some of the species in the vaccines are attenuated, egg-adapted and/or precocious lines, while others are strains that were originally isolated from commercial poultry production facilities. While all of these vaccines provide solid immunity to coccidial infection when applied carefully under good rearing conditions, especially in replacement and breeding flocks, these vaccines have not been universally accepted by the U.S. poultry industry for meat-producing broiler and heavy roaster bird flocks. The two major reasons for this reluctance has been (1) that bird performance, as measured by weight gain and feed efficiency, has not always equaled that seen with prophylactically medicated birds and (2) that reports of immunological variability of *E. maxima*, one of the major pathogenic and economically important coccidial species, indicate that vaccination with a given suspension of live oocysts may not be effective in protecting against field strains In differing geographical locations (Long et at 1986. *Avian Pathol.* 15: 217–278; Long et al., 1979. Parasit. 79: 451–457; Rose, M. E. 1982. In: *The Biology of the Coccidia*, P. L. Long, Ed., University Park Press, Baltimore Md., pages 329–371; Fit-Coy, S. H. 1992. Avian Dis. 36: 40–43; Lee, E.-H. 1993. In; *Proceedings of the Vith International Coccidiosis Conference*, Barta and Fernando, Eds., University of Guelph, Guelph, Ont., Canada, pages 118–121).

Danforth et al. described the effect of immunization with oocysts on weight gain and feed conversion in two separate battery trials (Danforth et al. 1997. *Avian Dis.* 41: 792–801). Three different strains of chickens of either sex were immunized by oral gavage at 1 day of age. Each bird was immunized with 2500 oocysts of a virulent field strain isolate of Eimeria maxima and challenged with 25,000 oocysts of the same strain at 10 days of age. All immunized birds of all strains had significantly higher average weight gains and lower lesion scores at 7 days post-challenge (PC) than that seen in the non-immunized, challenged groups. However, feed conversions were lower for the the immunized groups than the non-immunized birds. All immunized birds, except for strain females, had significantly higher average weight gains than the non-immunized, challenged birds for the length of the experiment (1–17 days of age). None of the immunized birds had significantly higher average weight gains than the non-immunized, unchallenged groups for the entire experiment. These results are in general accord with studies reported previously which indicated that immunization of 1-day-old broiler chicks with oocysts would elicit partial protection against challenge by the same species (Bafundo, K. W. 1989. *INRA, Tours*, 395–400; Long et al. 1986, supra).

The immunization of 2500 oocysts/bird did however depress weight gains of the birds in both battery trials at 10 days of age. Similar observations were seen for average weight gains (1–17 days of age) of immunized birds irrespective of challenge. The results of preliminary work carried out in caged battery trials indicated that an immunizing dose of 2500 oocysts/bird was necessary to elicit consistent and significant protection against challenge; doses of 500 or 1000 oocysts did not always reduce the severity of the mid-intestinal lesions, or protect against weight loss. Seemingly, the loss in productivity caused by the high immunization dose could not be made up within the first 17 days of age.

At the present time, less than 7% of all broiler meat birds produced in the U.S. (approximately 500,000,000 out of over 7.5 billion birds processed annually) use live oocyst vaccines. This is because of limited effectiveness against field strains of coccidia present in commercial grow-out facilities. For example, the strain of *E. maxima* present in one of the anti-coccidial vaccines, Immucox® as an example, does not always elicit sufficient immunity when challenged with heterologous field strains of this species (Lee, supra). Immucox® vaccine primarily incorporates strains from Canada. Recent work has shown considerable immunovariation in five strains of *E. maxima* taken from different geographical areas of North America (Martin et al. 1997. *Int. J. Parasitol.* 5: 527–533). Immunization with the Guelph laboratory strain *E. maxima*-GLP, a Canadian isolate, was 97% protective for homologous challenge, but had only 3% and 46% effectiveness in reduction of lesion scores after challenge with a U.S. isolate from Maryland, i.e., the USDA laboratory strain 68, and strain FL, a U.S. isolate from Florida, respectively. Immunization with strain 68 or FL protected against homologous challenge only (65% and 80%, respectively). Immunization with strain MD (another strain from Maryland) and NC (from North Carolina) protect against both homologous (88% and 69%, respectively) and heterologous challenge with the *E. maxima*-GLP, i.e., 85% and 74%.

These results suggest that Immucox® may not afford protection against challenge with certain strains of *E. maxima* present in the field (Danforth et al. 1997. *Parasitol. Res.* 83: 445–451; Martin et al., supra). This was confirmed when caged battery broiler birds were immunized by gavage with Immucox® and challenged with *E. maxima* strain MD; there was no protection with regard to either weight gain or lesion scores (Danforth et al. 1997, supra). However, if *E. maxima* strain MD was included in the Immucox® vaccine, then lesion scores resulting from challenge were reduced and weight gain was increased during challenge and throughout the entire experiment (Danforth, H. D. 1998. *Int. J. Parasitol.* 28: 1099–1109).

Based on these caged battery results, floorpen cage studies were used to measure the performance (as measured by average weight gain and feed conversion) of male roaster birds vaccinated by gel-delivery (IG12) with a reformulated Immucox® vaccine (containing the four original vaccine species, *E. acervulina, E. maxima, E. necatrix* and *E. tenella*, and oocysts of strain MD *E. maxima*) against absolute non-immunized-unchallenged (NINC), gavage-immunized with the reformulated vaccine (IGa2) and nicarbazin-narasin/narasin (Maxiban® and Monteban®, Elanco Products Co.) medicated (NIN/N) control groups. All birds were exposed to wood-shaving litter in the floorpens seeded with 2000 oocysts of strain MD *E. maxima*/g of litter. The gel-immunized birds performed as well as the anticoccidial-medicated non-immunized groups at the end of a 70 day growout period (Danforth 1998, supra).

In subsequent field trials, the same strain of male roaster birds immunized by gel-delivery at the hatchery with the reformulated Immucox® vaccine, performed similarly to non-immunized birds in control houses that had been medicated with the anticoccidial compound salinomycin (Sacox®, Hoechst Roussel Agri-Vet Co.). The immunized birds were again lighter at 4–5 weeks of age than the control birds, but were heavier by the time of processing (9–10 weeks of age). At the time of processing, adjusted feed conversions for the immunized birds averaged 3.75 points lower than those of the control, medicated birds. (Feed conversion was adjusted to an 8 lb bird using 5 points weight, i.e., 0.01 lb above 8 lb=1 pt.) In addition, total mortality in the immunized birds was lower for the entire growout than that seen in the controls. These results showed that a reformulated Immucox® viable oocyst vaccine, gel-delivered to 1 Day old birds, could control coccidiosis in commercial poultry operations and result in performance that was equal to, or better than, the anticoccidial-medicated birds.

Clearly, while available methods for the control of coccidiosis have met with success, the need for a vaccine that is capable of combating avian coccidiosis by effectively protecting against all field strains of *Eimeria maxima* remains. Improvement of live oocyst vaccine efficacy by the addition of immunovariant strains of coccidia would give better effective control of this economically important parasitic disease.

SUMMARY OF THE INVENTION

We have discovered that the addition of an immunologically selected immunovariant strain of *Eimeria maxima* to live oocyst vaccine increases the effectiveness of the vaccine against immunovariant strains of *E. maxima* that could be present in broiler grow-out houses by eliciting a more uniform immunological protection against coccidial infection.

In accordance with this discovery, it is an object of the invention to provide a novel immunovariant strain isolated by a novel process for obtaining a virulent non-crossreactive strain. Utilization of the novel immunovariant strain results in the production of a novel effective vaccine while still ensuring weight gain and effective feed conversion.

In a preferred embodiment of the invention, the immunovariant strain is *E. maxima*-1.

Other objects and advantages of the invention will become readily apparent from the following description.

DETAILED DESCRIPTION OF THE INVENTION

Figure 1A:
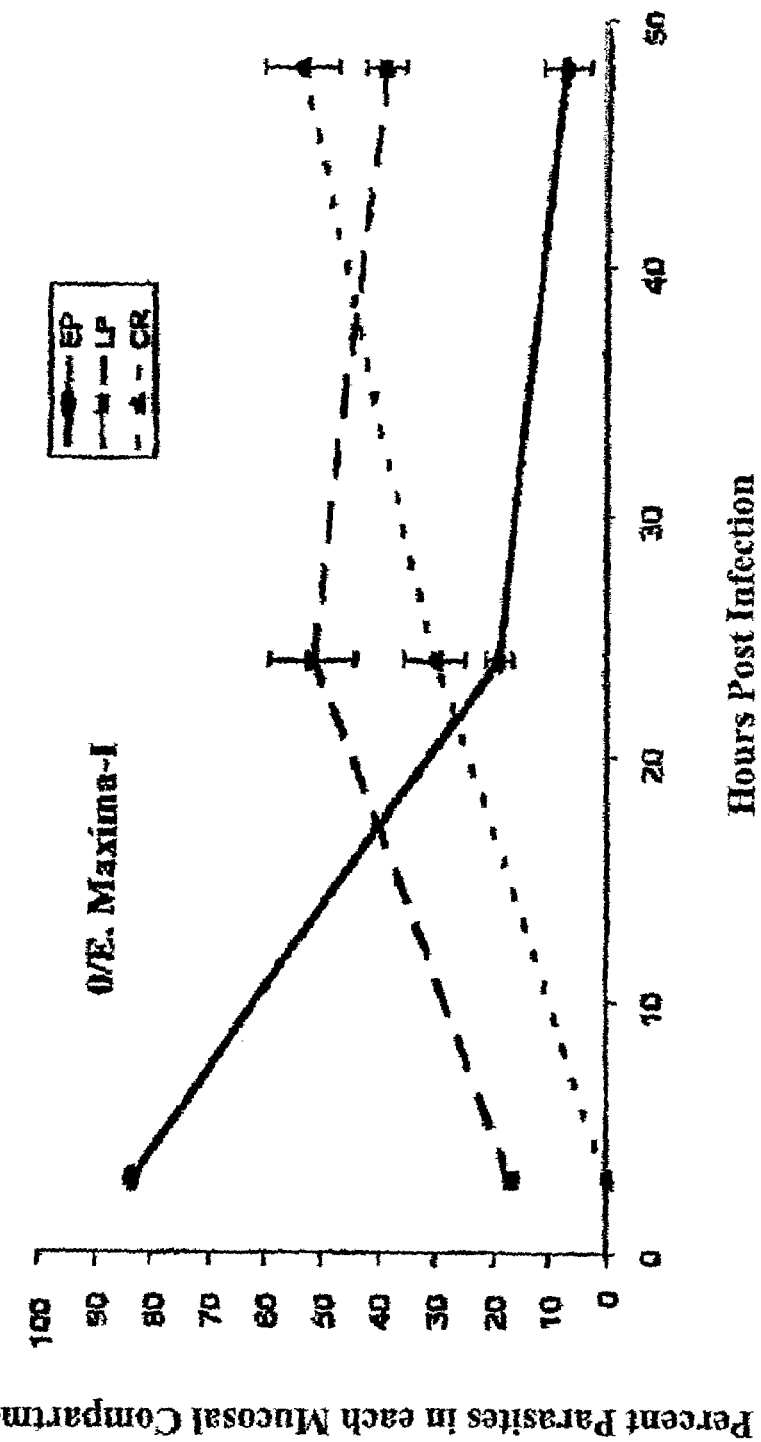
FIGS. 1A–1F depict the transport of *E. maxima* sporozoites through the intestinal mucosa over a period of 50 hours post challenge in groups of naïve chickens or chickens immunized with *E. maxima*-GPL or the immunovariant strain *E. maxima*-I challenged with either the homologous or heterologous strain of *E. maxima*. The percentage of parasites in each mucosal compartment: epithelial cells ♦—♦, lamina propria ■ - - - ■, and crypt ▲-----▲, were recorded at 3, 7, 24, 36, and 48 hr post challenge.
Figure 1B:
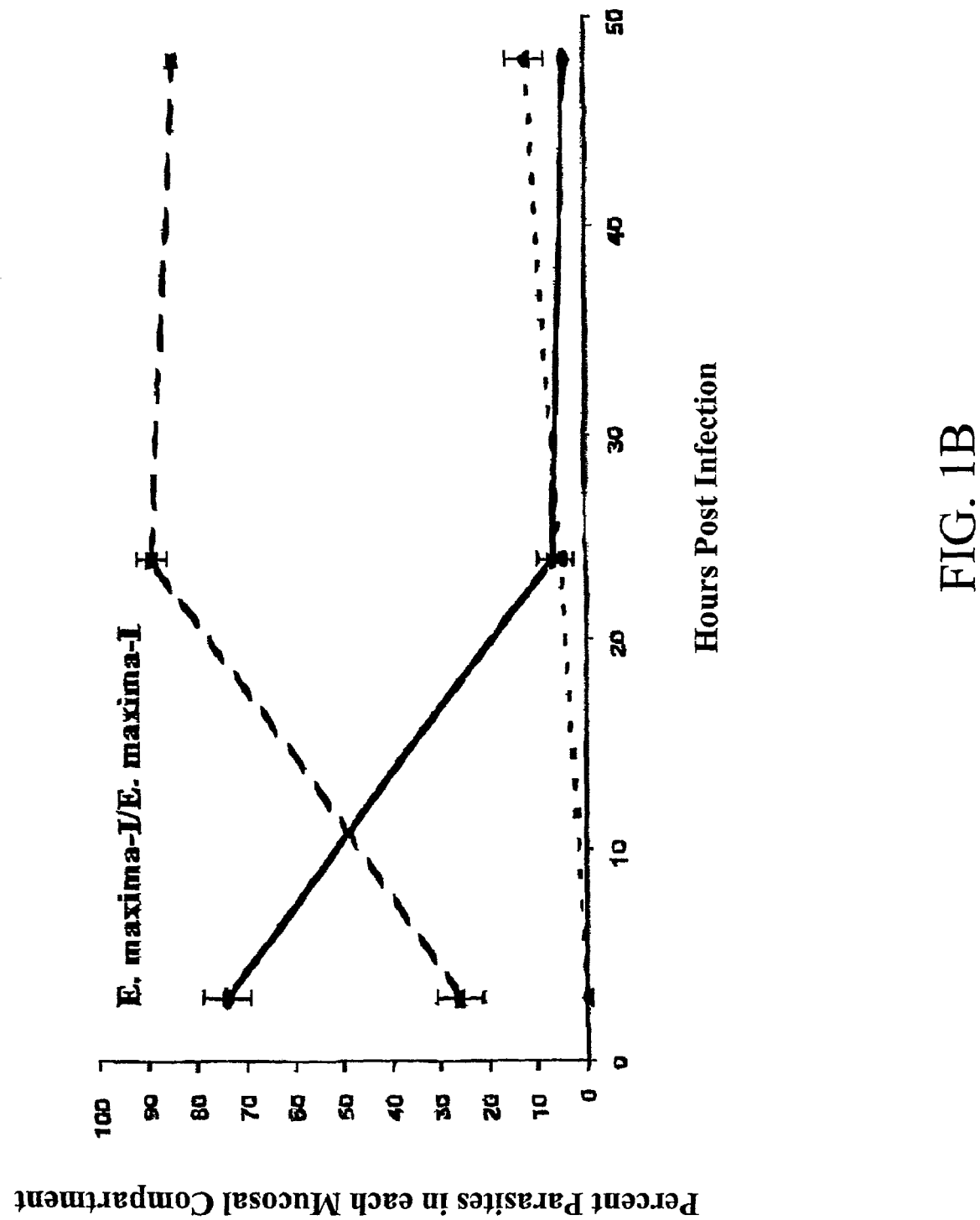
Figure 1C:
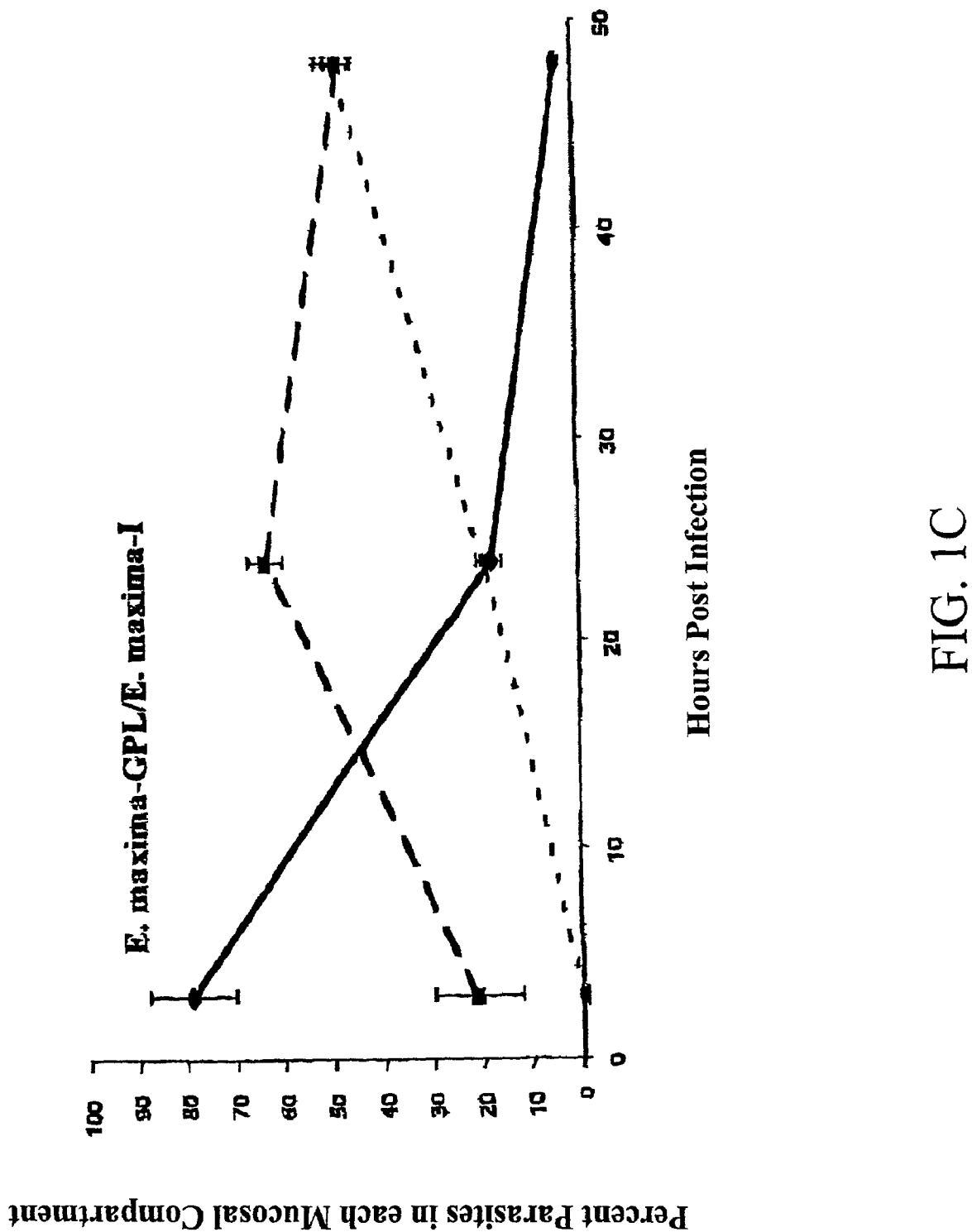
Figure 1D:
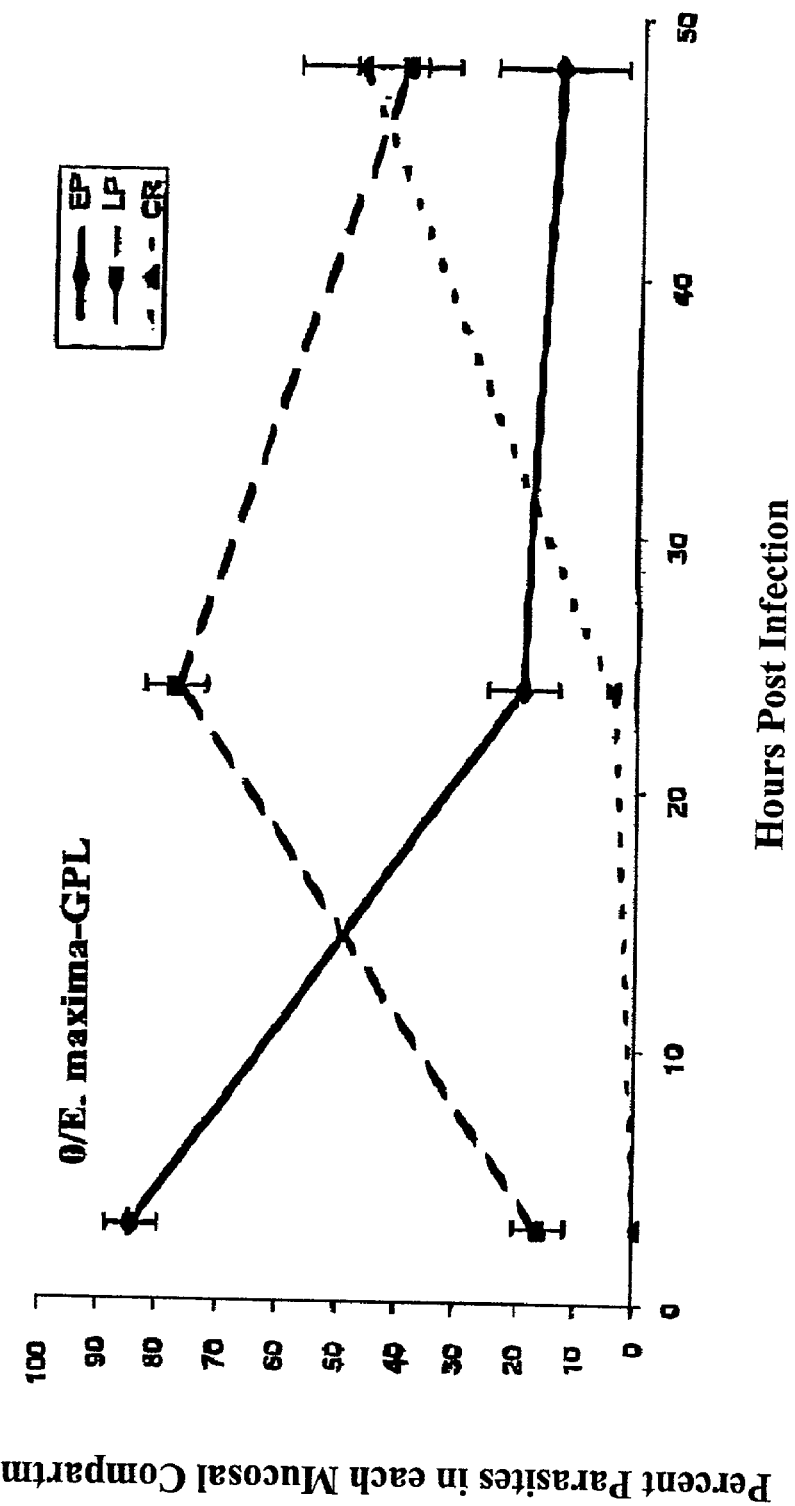
Figure 1E:
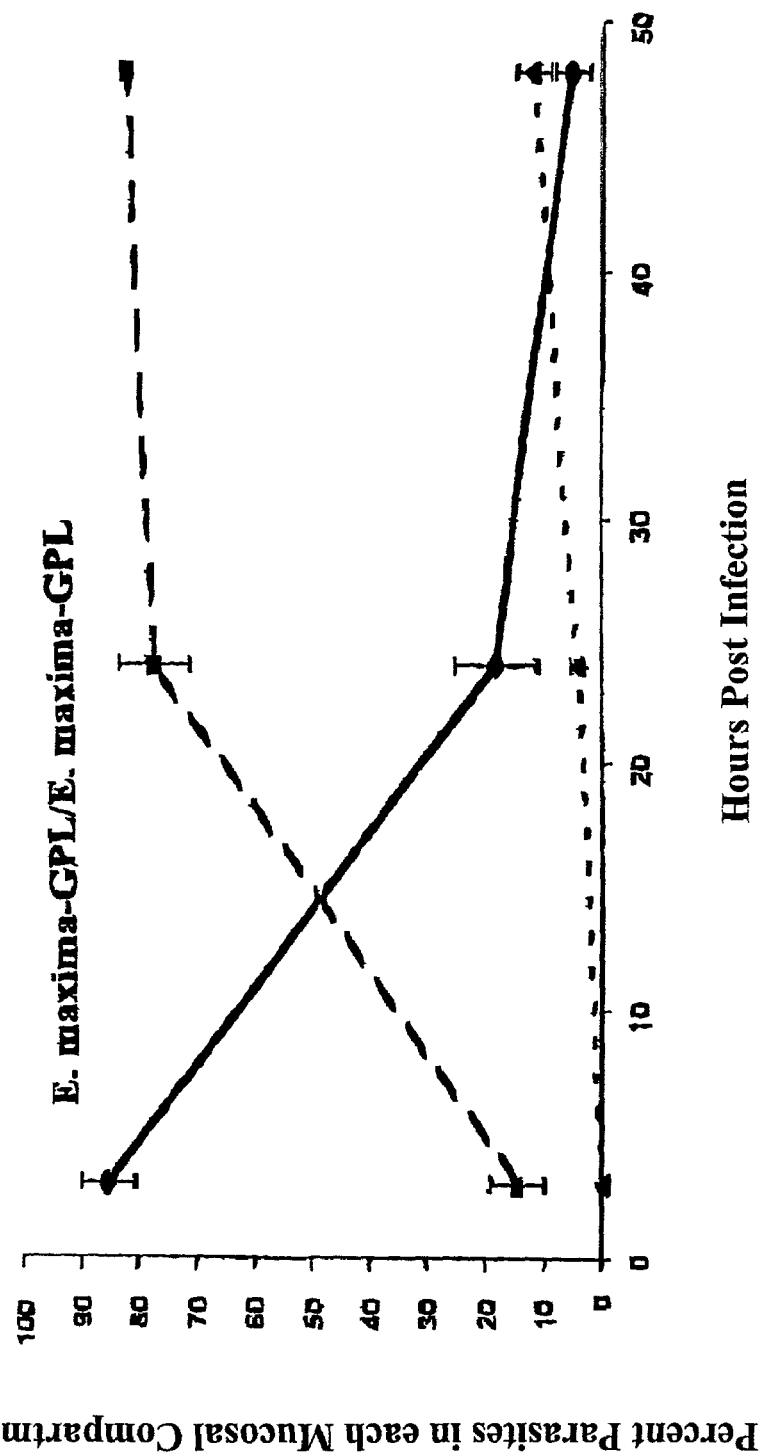
Figure 1F:
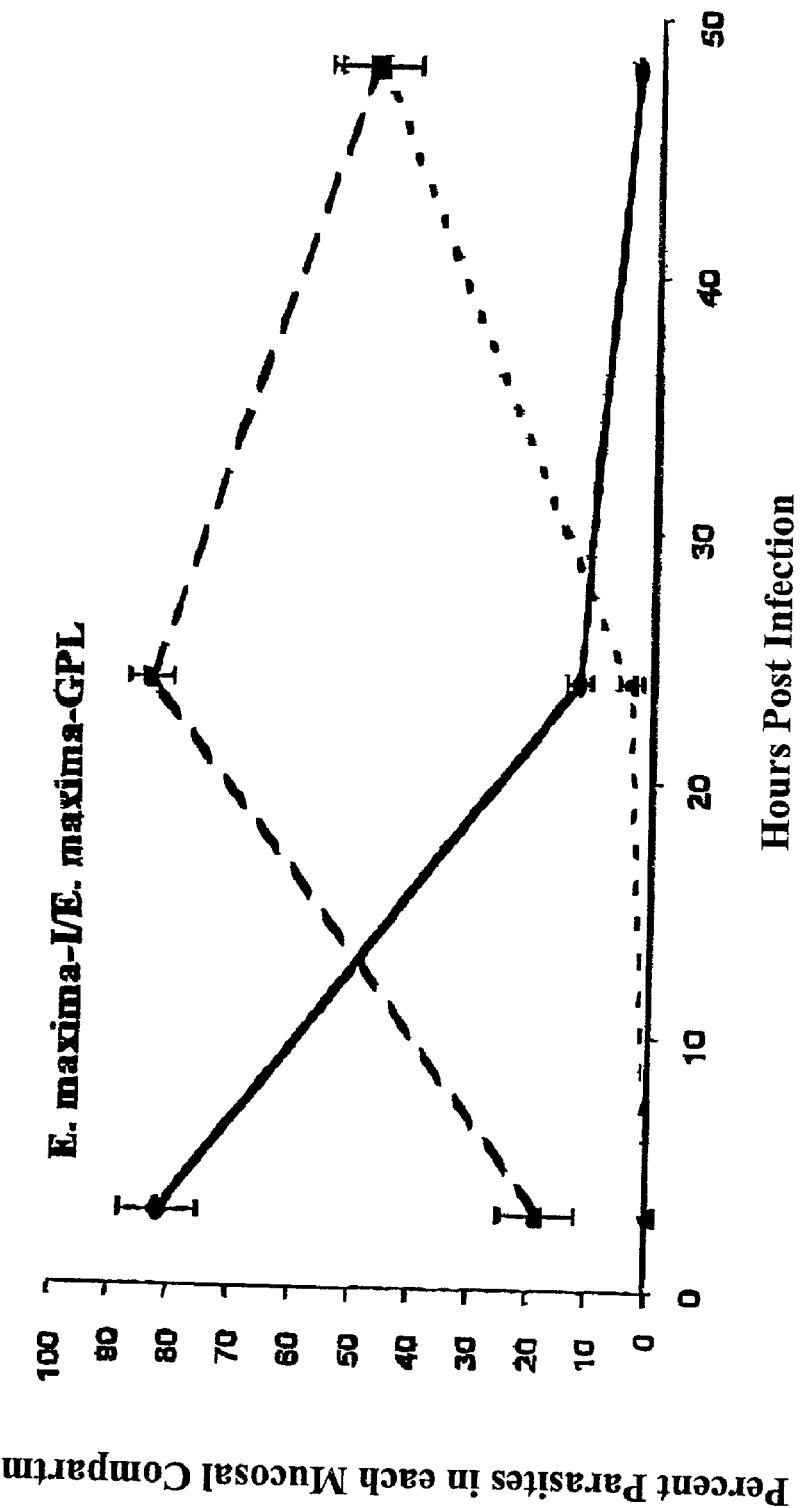

The Guelph laboratory strain, *E. maxima*-GLP, and USDA laboratory strain 68 have been maintained at the Ontario Veterinary College, Guelph, Canada, since 1973, and at the USDA, Beltsville, Md., since 1980, respectively. Outbreaks of Eimeria maxima were identified in a number of flocks where live vaccination or anti-coccidial medication was being used for control of coccidiosis. Litter collected at these sites was examined for the presence of coccidial oocysts and *E. maxima* was isolated using micromanipulation.

Three strains, MD, NC, and FL, were isolated from litter samples collected in commercial broiler houses in Maryland, North Carolina, and Florida, respectively, during 1994 and 1995 (Martin et al., supra). As one of the most immunogenic species of coccidia in birds, *E. maxima* is normally capable of eliciting nearly complete protection against homologous challenge even after a single exposure to a modest number of infective oocysts.

During the early part of an infection with *E. maxima*, the excysted sporozoites enter villus epithelial cells of the small intestine and are transported via mononuclear cells to the crypt epithelium where they initiate merogony (schizogony; Riley et. al. 1988. *J. Parasitol.* 74: 103–110). When birds immunized with *E. maxima* are challenged with the homologous strain, sporozoites tended to penetrate the epithelium normally and to enter mononuclear cells, but were impeded from further migration past the lamina propria, presumably as a result of immune recognition.

However, one of the isolated strains, the Florida strain, was found to only partially protect chickens against subsequent challenge with the Guelph laboratory strain of *E. maxima* and vice versa. To confirm that the Florida strain was actually *E. maxima*, the strain was characterized biologically. Oocyst morphology (color and dimensions) and life cycle features (number of asexual generations, their locations, and morphology) all confirmed that the isolated parasites were *E. maxima*. In addition, molecular analyses utilizing protein profiles, random amplified polymorphic DNA-PCR analysis, and DNA sequences obtained from the internal transcribed spacer regions of the rRNA genes, confirmed that these strains were all *E. maxima* (Barta et al. 1998. *Int. J. Parasitol.* 28: 485–492).

The question arose as to whether the lack of complete cross protection between the Florida and Guelph strains of *E. maxima* was manifested at the level of sporozoite transport. To assess this, we examined the transport of *E. maxima* sporozoites through the intestinal mucosa over a period of 72 hours post challenge in groups of naïve or immunized (previously infected with *E. maxima*) chickens challenged with either the homologous or heterologous strain of *E. maxima*. In birds immunized and challenged with the homologous strain, sporozoites accumulated in the lamina propria and were blocked from further movement into the crypts by 72 hours post challenge. In naïve birds, fewer than 5 percent of sporozoites were found in the crypts by 72 hr post challenge. In immunized birds challenged with the heterologous strain, fewer sporozoites reach the crypts than in naïve birds but at least 4 times as many sporozoites successfully migrated to the crypts when compared with birds challenged with the homologous strain. The degree of cross-protection afforded by the heterologous strain as measured by sporozoite transport success was not equally reciprocal; birds immunized with the Guelph strain were not protected against challenge with the Florida strain, however, the Florida strain did partially protect the birds against challenge with the Guelph strain. This lack of reciprocity stimulated us to attempt in vivo selection of a Florida strain that would have no detectable immunological cross reactivity with the Guelph strain.

Shed oocyst counts and the measured parameters of (1) intestinal lesion scores, (2) average weight gain during challenge infection, (3) average weight gain from boost to termination of the experiment, and (4) feed conversions were used to determine the ability of individual strains of *E. maxima* to elicit cross-immunity in response to challenge by various *E. maxima* strains.

The invention includes the immunovariant strain *E. maxima*-I, exemplified in Examples 3–6, individually and its use in vaccinating chickens against a coccidial infection. In a preferred embodiment, the present invention encompasses any strains that correspond in characteristics to the line *E. maxima*-I and other strains derived according to the immunological selection method of the invention. The invention includes such sub-lines of the above strain (having been derived from the same parent) or descendants therefrom (having been derived from the deposited lines by further passaging). The immunovariant strain of the invention can be used individually or in any combination of the strain of the invention with one or more other live or attenuated *Eimeria* organisms, in any proportions. The invention further includes feed or drink, including water, containing parasites of the line.

The vaccine according to the invention can be administered in a conventional active immunization scheme: single or repeated administration in a manner compatible with the dosage formulation, and in such amount as will be prophylactically effective, i.e. the amount of immunizing antigen capable of expressing said antigen that will induce immunity in poultry against challenge by virulent *Eimeria* parasites. Immunity is defined as the induction of a significant level of protection in a population of chickens after vaccination compared to an unvaccinated group. The effective amount will vary with the particular target animal, its age and size, and may be readily determined by the practitioner skilled in the art. Suitable regimes for initial administration and boosters will also be variable, but may be typified by an initial administration followed by subsequent inoculations or other administrations.

A "dose" of vaccine is the amount provided for one bird. In general, the total number of sporulated oocysts per dose of vaccine may vary between about 2500 and 50,000.

Next to an increase in protection, a vaccine comprising the immunovariant strain of the invention will also reduce the number of oocysts shed by the infected animals. Normally, the shed oocysts will infect other animals in the flock. A decrease in the number of oocysts shed will then also give a decrease in the number of animals which are subsequently infected and also a decrease in the number of oocysts shed will give rise to a lesser infective load.

Vaccination with live oocysts requires an efficient and practical delivery system that will synchronously expose all birds in a flock to a small uniform number of parasites.

Delivery systems include: crop gavage, gel-delivery system, slurry delivery, floor pen feed delivery, and spray cabinet. The spray cabinet method is the preferred method of the invention. In the spray cabinet delivery system, the dosage can be given 1×. Birds, in the process of preening ingest the oocysts. The use of the vaccine according to the invention is particularly valuable in treating fowls intended for breeding and the production of heavy broilers (e.g. fowls reared for 55 days or longer).

Typically, such vaccines are prepared as liquid solutions or suspensions, solid forms suitable for solution in, or suspension in, liquid prior to injection may also be prepared. The oocysts may be administered to a target animal in the presence of a physiologically acceptable diluent. The oocysts of the present invention may be stored under refrigeration; sporocysts and sporozoites can be frozen.

Additionally the vaccine may also contain an aqueous medium or a water containing suspension, often mixed with other constituents in order to increase the activity and/or the shelf life. These constituents may be salts, pH buffers, stabilizers (such as skimmed milk or casein hydrolysate), emulsifiers, adjuvants to improve the immune response (e.g. oils, muramyl dipeptide, aluminium hydroxide, saponin, polyanions and amphipatic substances) and preservatives.

A vaccine comprising the immunovariant strain of the invention may also comprise other immunogenic proteins of *E. maxima* or immunogenic proteins of other Eimeria species. Such a combination vaccine will decrease the parasitic load in a flock of poultry and will increase the level of protection against coccidiosis.

It is clear that a vaccine according to the invention may also contain immunogens related to other pathogens of poultry, or may contain nucleic acid sequences encoding these immunogens, like antigens of Marek's Disease virus (MDV), Newcastle Disease virus (NDV), Infectious Bronchitis virus (IBV), Chicken Anemia Agent (CAA), Reovirus, Avian Retrovirus, Fowl Adenovirus, Turkey Rhinotracheitis virus or *E. coli* to produce a multivalent vaccine. Birds receiving vaccine may advantageously be fed one or more antibiotic growth promoters such as avoparcin and virginiamycin.

The *Eimeria* strain *Eimeria maxima*-I has been deposited with the American Type Culture Collection (ATCC), 10801 University Blvd., Manassas, Va. 20110-2209 on Jul. 25, 2002 under accession number PTA-4959 as a patent deposit under the Budapest Treaty on the International Recognition of the Deposit of Microorganisms for the Purposes of Patent Procedure. The subject strain has been deposited under conditions that assure that access to the strain will be available during the pendency of this patent application to one determined by the Commissioner of Patents and Trademarks to be entitled thereto under 37 CFR 1.14 and 35 USC 122. The deposit is available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject strain deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least 30 (thirty) years after the date of deposit or for the enforceable life of any patent which may issue disclosing the strain. The depositor acknowledges the duty to replace the deposit should the depository be unable to furnish a sample when requested, due to the condition of the deposit. All restrictions on the availability to the public of the subject strain deposit will be irrevocably removed upon the granting of a patent disclosing it.

EXAMPLES

The following examples serve as further description of the invention and methods for practicing the invention. They are not intended as being limiting, rather as providing guidelines on how the invention may be practiced.

Example 1

Preparation of Parasites

Coccidial oocysts of *E. maxima* strains were purified free of bacterial and fungal contamination by treatment with 5.25% sodium hypochlorite solution at 0°–4° C. for 15 min followed by extensive washing with cold water. Oocysts were then separated from other debris by centrifugation over a cushion of 0.6M sucrose in a Sorvall HB-4 rotor for 5 min at 5000 rpm at 40° C. Oocysts float on top of the cushion while most of the other debris is pelleted at the bottom of the centrifuge tube. The purified oocysts were again washed thoroughly with cold water and were stored at 4° C. in Hank's medium containing 10 units/ml penicillin and 10 µg/ml streptomycin.

For all strains except GPL, at least 40 *E. maxima* oocysts identified by size and yellowish oocyst walls were isolated using hand-drawn pipettes attached to a micromanipulator, pooled, and passaged twice through coccidia-free chickens to obtain a sufficient quantity of sporulatd oocysts. All strains were confirmed to be *E. maxima* by microscopic examination and isoenzyme analysis (data not shown) prior to use.

Example 2

Cross-immunity Trials with *E. maxima*-GLP and *E. maxima*-I

One-day-old male chickens of a roaster line were obtained. All chicks had been vaccinated at the hatchery against Marek's disease, Newcastle disease and infectious bronchitis. To immunize against E. maxima, chicks were randomly selected and placed 10 per cage in battery brooder cages at 1 day of age and inoculated orally with 2500 oocysts of individual strains of *E. maxima* in 0.1 ml water or with 0.1 ml water as sham inoculated controls. Feed and water were available ad libitum throughout the experiment. At 10 days of age, chicks were challenged orally with 25,000 oocysts of each strain of *E. maxima* in 1 ml water or given 1 ml water as unchallenged controls.

Chicks were euthanized 6 days after challenge and the intestines were examined for coccidial lesions (Johnson & Reid. 1970. *Exp. Parasitol.* 28: 30–36). Individual body weights were obtained on the day of challenge (10 days of age) and 6 days later in order to calculate weight gain during the challenge.

Example 3

In vivo Selection of the Immunovariant Strain *E. maxima*-I

Birds immunized by oral infection with the Guelph strain of *E. maxima* (*E. maxima*-GLP) were challenged with the Florida strain. The resulting oocysts were sporulated and then passaged through additional birds immunized against the Guelph strain. Four such passage collections, using oocysts collected from each preceding passage, were used to challenge the next group of immunized birds and selected for a strain of *E. maxima*, designated *E. maxima*-I, that was totally immunovariant from the *E. maxima*-GPL. Birds immunized against the Guelph strain no longer recognized the resulting immunovariant *E. maxima* strain, *E. maxima*-I.

Example 4

Analysis of Parasite Movement Through Mucosal Compartments

This lack of immunological recognition was assessed by comparing oocyst output (Example 4) and sporozoite transport in naïve and Guelph strain-immunized birds that were then challenged with *E. maxima* —I, the immunovariant strain of *E. maxima* (FIGS. 1D and 1F, respectively). In both cases, the derived parasite strain, *E. maxima*-I, behaved similarly in both the Guelph strain-immunized and naïve birds suggesting that all or most immunologically relevant cross reactive epitopes had been selected against and removed from the Florida strain.

Example 5

Effectiveness of Strains E. maxima-GLP and *E. maxima*-I in Eliciting Cross-Protection or Protection Against Homologous Challenge For cross-immunity trials, groups of approximately 50 chicks were each inoculated at 1 day of age, as described in Example 2, with the *E. maxima*-GPL strain or the immunovariant strain, *E. maxima*-I. An additional group of 50 chicks were sham inoculated. Within each inoculated group, 9–10 birds were challenged with each strain of *E. maxima*. Likewise, the sham inoculated birds were divided into subgroups of 9–10 and each was challenged with one of the strains of *E. maxima*; these birds represented sham inoculated/challenged controls. In addition, 28 chicks served as sham inoculated, sham challenged controls.

Table 1 shows that *E. maxima*-GPL-immunized birds shed as many oocysts after challenge with the *E. maxima*-I strain as did the non-immunized birds challenged with *E. maxima*-I, indicating no cross-protection. In contrast, the *E. maxima*- GPL- and *E. maxima*-I-immunized birds shed zero or very few oocysts after homologous challenge.

TABLE 1

Number of Oocysts Produced Per 24 hr By Chickens After Various Treatments

| Treatment | | | Days Post Challenge | | | | |
|---|---|---|---|---|---|---|---|
| Immunize | Challenge | G | 4–5 | 5–6 | 6–7 | 7–8 | 8–9 |
| E. maxima-GPL | E. maxima-GPL | 1 | 0 | 0 | 0 | 0 | 0 |
|  |  | 2 | 0 | 0 | 0 | 0 | 0 |
|  |  | 3 | 0 | 0 | 0 | 0 | 0 |
|  | Total |  | 0 | 0 | 0 | 0 | 0 |
| E. maxima-I | E. maxima-I | 1 | 0 | 84 | 45 | 0 | 0 |
|  |  | 2 | 96 | 502 | 594 | 20 | 0 |
|  |  | 3 | 0 | 20 | 0 | 0 | 0 |
|  | Total |  | 96 | 586 | 659 | 20 | 0 |
| E. maxima-GPL | E. maxima-I | 1 | 192 | 329060 | 5930000 | 2470000 | 566842 |
|  |  | 2 | 0 | 89580 | 9980000 | 3090000 | 47466 |
|  |  | 3 | 0 | 782420 | 7370000 | 6300000 | 697994 |
|  | Total |  | 192 | 1201060 | 2328000 | 11860000 | 1312302 |
| Non immunized | E. maxima-I | 1 | 0 | 609190 | 6020000 | 5820000 | 249284 |
|  |  | 2 | 0 | 243900 | 7240000 | 5950000 | 407652 |
|  |  | 3 | 0 | 329270 | 3790000 | 7370000 | 519943 |
|  | Total |  | 0 | 1182360 | 17050000 | 19140000 | 1176879 |

Example 6

Effect of E. maxima strains on Weight Gain, Feed Conversion, and Cecal Pathology For this trial, groups of approximately 50 chicks were each inoculated at 1 day of age, as described in Example 2. Birds were first immunized with the E. maxima-GPL strain, the immunovariant strain, E. maxima-I, or a third E. maxima field strain (designated E. maxima-ESS) and then challenged with each of these three strains. Male birds were immunized with 100 oocysts/bird at 1 day of age or 1000 oocysts/bird at 10 days of age given by oral gavage and challenged with 25,000 oocysts of E. maxima-I/bird, 30,000 oocysts of E. maxima-GPL/bird, or 50,000 oocysts of E. maxima-ESS/bird at 20 days of age. In addition, birds immunized with a commercially available live oocyst vaccine COCCIVAC B® (American Scientific Laboratories, Millsboro, DE; 0.1 ml of 10 dose/ml) or the COCCIVAC B® vaccine (10 dose/ml) to which the E. maxima-I strain (1000 oocysts/ml; 0.1 ml/bird) was added, were also challenged with the three different E. maxima strains. Parameters measured were intestinal lesion scores, average weight gain during challenge infection, average weight gain from boost to termination of the experiment, and feed conversions (amount of feed consumed/weight gain). Table 2 shows the result for the parameters listed above after challenge of birds immunized with E. maxima-GPL, E. maxima-I, E. maxima-ESS, COCCIVAC B®D, or COCCIVAC B®-E. maxima-I with the three different strains of E. maxima.

TABLE 2

Caged Battery Trial Experiment Using Male Broiler Birds

| Treatment Immunize/Challenge | Avg Feed Conver. | Avg Lesion Score During Challenge* | Avg Wgt Gain During Challenge* | Avg Wgt Gain - End Challenge* |
|---|---|---|---|---|
| Non/Non | 1.74 | 0.00$^a$ | 373.47$^a$ | 903.04$^a$ |
| Non/E. maxima-I | 3.23 | 3.77$^b$ | 158.90$^c$ | 683.42$^c$ |
| Non/E. maxima-ESS | 1.96 | 3.31$^b$ | 294.44$^b$ | 816.31$^b$ |
| Non/E. maxima-GPL | 3.11 | 3.61$^b$ | 153.13$^c$ | 675.66$^a$ |
| COCCIVAC ®-E. maxima-I/Non | 1.75 | 0.08$^a$ | 361.61$^a$ | 860.64$^a$ |
| COCCIVAC ®-E. maxima-I/ E. maxima-GPL | 1.80 | 0.69$^b$ | 335.25$^a$ | 861.56$^a$ |
| COCCIVAC ®-E. maxima-I/ E. maxima-I | 1.81 | 0.00$^a$ | 342.43$^a$ | 860.12$^a$ |
| COCCIVAC ®-E. maxima-I/ E. maxima-ESS | 1.77 | 0.00$^a$ | 365.00$^a$ | 882.14$^a$ |
| E. maxima-I/Non | 1.69 | 0.07$^a$ | 388.93$^a$ | 912.86$^a$ |
| E. maxima-I/E. maxima-GPL | 1.86 | 1.37$^b$ | 327.74$^b$ | 833.64$^b$ |
| E. maxima-I/E. maxima-I | 1.68 | 0.00$^a$ | 371.69$^{ab}$ | 884.69$^{ab}$ |
| E. maxima-I/E. maxima-ESS | 1.81 | 0.00$^a$ | 347.48$^{ab}$ | 873.00$^{ab}$ |
| COCCIVAC ®/Non | 1.71 | 0.00$^a$ | 395.57$^a$ | 934.14$^a$ |
| COCCIVAC ®/E. maxima-GPL | 1.85 | 2.13$^b$ | 313.67$^b$ | 797.94$^c$ |
| COCCIVAC ®/E. maxima-I | 2.36 | 3.21$^c$ | 224.63$^c$ | 740.13$^c$ |
| COCCIVAC ®/E. maxima-ESS | 1.91 | 2.08$^b$ | 303.50$^b$ | 826.31$^b$ |
| E. maxima-GPL/Non | 1.79 | 0.00$^a$ | 367.42$^a$ | 888.90$^{ab}$ |
| E. maxima-GPL/E. maxima-GPL | 1.70 | 0.06$^a$ | 365.19$^a$ | 904.56$^a$ |

TABLE 2-continued

Caged Battery Trial Experiment Using Male Broiler Birds

| Treatment Immunize/Challenge | Avg Feed Conver. | Avg Lesion Score During Challenge* | Avg Wgt Gain During Challenge* | Avg Wgt Gain - End Challenge* |
|---|---|---|---|---|
| E. maxima-GPL/E. maxima-I | 1.92 | 2.25[b] | 306.88[b] | 828.19[b] |
| E. maxima-GPL/E. maxima-ESS | 1.79 | 0.64[a] | 334.36[ab] | 836.36[ab] |
| E. maxima-ESS/Non | 1.72 | 0.06[a] | 387.79[a] | 956.67[a] |
| E. maxima-ESS/E. maxima-GPL | 3.05 | 3.93[c] | 166.39[c] | 711.63[c] |
| E. maxima-ESS/E. maxima-I | 3.22 | 3.63[c] | 168.31[c] | 715.56[c] |
| E. maxima-ESS/E. maxima-ESS | 1.88 | 2.63[b] | 313.88[b] | 861.94[b] |

Based on the statistical analysis of these parameters, *E. maxima*-GPL immunization did not protect against *E. maxima*-I challenge, *E. maxima*-I immunization did not protect against *E. maxima*-GPL challenge, and *E. maxima*-ESS immunization did not protect against *E. maxima*-GPL, *E. maxima*-I, or even its homologous challenge with *E. maxima*-ESS. Birds immunized with COCCIVAC B® vaccine were not protected against challenge by any of the three *E. maxima* strains even though the vaccine did contain its own strain of *E. maxima*. However, the addition of the *E. maxima*-I strain to the COCCIVAC B® vaccine did significantly protect the immunized birds against challenge with the three different *E. maxima* strains. Addition of the *E. maxima*-I strain to the live oocyst vaccine increased the effectiveness of the vaccine against immunovariant strains of *E. maxima* that could be present in broiler grow-out houses by eliciting a more uniform immunological protection against coccidial infection.

All publications and patents mentioned in this specification are herein incorporated by reference to the same extent as if each individual publication or patent was specifically and individually indicated to be incorporated by reference.

It is understood that the foregoing detailed description is given merely by way of illustration and that modifications and variations may be made therein without departing from the spirit and scope of the invention.

We claim:

1. A variant strain of *Eimeria maxima*, said variant strain is designated *E. maxima*-I and is deposited under the ATCC accession number PTA-4959.

2. The variant strain *E. maxima*-I (ATCC number PTA-4959) of claim 1 which is further identified by the characteristic wherein: immunization with *E. maxima*-I (ATCC number PTA-4959) protects against challenge with *E. maxima*-I (ATCC number PTA-4959) but does not protects against challenge with the Guelph strain of *E. maxima*, designated *E. maxima*-GLP, an indication that *E. maxima*-I (ATCC number PTA-4959) has no detectable immunological cross reactivity with *E. maxima*-GLP.

* * * * *